(12) United States Patent
Chen et al.

(10) Patent No.: US 11,948,288 B2
(45) Date of Patent: Apr. 2, 2024

(54) MOTION ARTIFACTS SIMULATION

(71) Applicant: Shanghai United Imaging Intelligence Co., Ltd., Shanghai (CN)

(72) Inventors: Xiao Chen, Lexington, MA (US); Shuo Han, Baltimore, MD (US); Zhang Chen, Brookline, MA (US); Shanhui Sun, Lexington, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 361 days.

(21) Appl. No.: 17/340,635

(22) Filed: Jun. 7, 2021

(65) Prior Publication Data

US 2022/0392018 A1    Dec. 8, 2022

(51) Int. Cl.
*G06T 5/70* (2024.01)
*G06N 3/08* (2023.01)
*G16H 30/20* (2018.01)
*G16H 30/40* (2018.01)
*G16H 50/20* (2018.01)
*G16H 50/50* (2018.01)
*G16H 50/70* (2018.01)

(52) U.S. Cl.
CPC ............... *G06T 5/70* (2024.01); *G06N 3/08* (2013.01); *G16H 30/20* (2018.01); *G16H 30/40* (2018.01); *G16H 50/20* (2018.01); *G16H 50/70* (2018.01); *G06T 2207/10088* (2013.01); *G06T 2207/20056* (2013.01); *G06T 2207/20081* (2013.01); *G06T 2207/20084* (2013.01); *G16H 50/50* (2018.01)

(58) Field of Classification Search
None
See application file for complete search history.

(56) References Cited

U.S. PATENT DOCUMENTS 6,341,179 B1 * 1/2002 Stoyle ................. G06T 11/008
                                                        382/254
8,191,359 B2    6/2012 White et al.
(Continued)

FOREIGN PATENT DOCUMENTS

CN           110940943 A      3/2020
WO    WO-2019086284 A1 *   5/2019    ......... G01R 33/5608

*Primary Examiner* — Jiangeng Sun
(74) *Attorney, Agent, or Firm* — Zhong Law LLC

(57) ABSTRACT

Motion contaminated magnetic resonance (MR) images for training an artificial neural network to remove motion artifacts from the MR images are difficult to obtain. Described herein are systems, methods, and instrumentalities for injecting motion artifacts into clean MR images and using the artificially contaminated images for machine learning and neural network training. The motion contaminated MR images may be created based on clean source MR images that are associated with multiple physiological cycles of a scanned object, and by deriving MR data segments for the multiple physiological cycles based on the source MR images. The MR data segments thus derived may be combined to obtain a simulated MR data set, from which one or more target MR images may be generated to exhibit a motion artifact. The motion artifact may be created by manipulating the source MR images and/or controlling the manner in which the MR data set or the target MR images are generated.

20 Claims, 8 Drawing Sheets

(56) References Cited

U.S. PATENT DOCUMENTS

| | | | |
|---|---|---|---|
| 9,341,693 B2* | 5/2016 | Xue | G01R 33/56509 |
| 10,698,063 B2 | 6/2020 | Braun et al. | |
| 2007/0036418 A1* | 2/2007 | Pan | A61B 6/027 |
| | | | 382/131 |
| 2012/0235679 A1* | 9/2012 | Xue | G01R 33/56509 |
| | | | 324/307 |
| 2013/0051644 A1* | 2/2013 | Nett | G06T 11/005 |
| | | | 382/131 |
| 2016/0324500 A1 | 11/2016 | Fan et al. | |
| 2019/0128989 A1* | 5/2019 | Braun | G06N 3/047 |
| 2019/0377047 A1* | 12/2019 | Chen | G01R 33/5608 |
| 2020/0160741 A1* | 5/2020 | Cadwell | A61B 5/4041 |

* cited by examiner

MOTION ARTIFACTS SIMULATION

BACKGROUND

Motion artifacts such as those caused by the respiratory movements of patients are commonly encountered in Magnetic Resonance Imaging (MRI) procedures, especially those involving dynamic scan subjects (e.g., the heart). It has been reported that about 20% of repeated MRI scans are attributable to motion artifacts, which imposes significant burdens on hospitals and other medical facilities. On the other hand, even though deep learning based techniques have brought great progress to MRI image analysis and post-processing, motion artifact removal remains a challenging task. A major roadblock is the lack of training data. Motion contaminated images are usually discarded after the scanning, and it is even harder to collect data with controlled motions, such as image pairs consisting of clean and motion-contaminated images that can be used for supervised learning.

Accordingly, systems, methods, and instrumentalities are desirable to generate magnetic resonance (MR) images with simulated motion artifacts. These motion contaminated MR images may then be used to tackle a wide range of problems including, for example, training an artificial neural network to automatically remove motion artifacts from MR images.

SUMMARY

Described herein are systems, methods, and instrumentalities for injecting motion artifacts into magnetic resonance (MR) images to create artificially contaminated MR images that can be used for various purposes. The motion contaminated MR images may be created based on a set of source MR images of a scanned object that are substantially free of motion artifacts. The source MR images may include multiple sub-sets of images and each of the subsets may be associated with one of multiple physiological cycles of the scanned object such as one of multiple cardiac cycles. From the sub-set of source MR images associated with a physiological cycle or a modified version of the sub-set of source MR images associated with the physiological cycle, a (e.g., at least one) MR data segment may be derived for the physiological cycle. Motion artifacts may be introduced at this stage based on a motion pattern (e.g., an artificially created motion pattern) that represents the motion artifacts. For example, the artifacts may be introduced by deforming the sub-sets of source MR images based on the motion pattern, by reordering at least a portion of the source images, by interpolating a portion of the source images to derive one or more additional source MR images, etc. The MR data segments derived for the multiple physiological cycles may be combined to obtain an MR data set (e.g., a simulated MR data set) resembling that acquired from a practical MR procedure. Using this MR data set (e.g., a selected portion of the MR data set), one or more target MR images may be generated to include a certain motion artifact. For example, to simulate a mis-triggering artifact, the one or more target MR images may be generated such that they may be associated with two or more of the physiological cycles and may appear to have been captured with a missed trigger.

In examples, the MR data segments associated with the multiple physiological cycles may be combined (e.g., using a line-by-line Cartesian method) to obtain the MR data set (e.g., digitized MR signals) from which the target images may be generated. In examples, combining the MR data segments may include interpolating the MR data segments to simulate a top-down sampling of MR signals. In examples, the MR data segments derived for the multiple physiological cycles may include k-space data obtained by applying Fast Fourier Transform (FFT) to the source MR images (or a modified version thereof). Such k-space data may represent, for example, the spatial frequency and/or phase information of an object captured in a practical MRI procedure.

In examples, generating the one or more target MR images based on the simulated MR data set (e.g., k-space data) may comprise applying inverse FFT (iFFT) to at least a portion of the MR data set to derive a target MR image. In examples, generating the one or more target MR images based on the simulated MR data set may comprise interpolating portions of the k-space data to cover a portion or the entirety of the k-space. In examples, the one or more target MR images may be generated further based on one or more coil sensitivity maps.

The MR images generated using the systems, methods, and instrumentalities described herein may be used for different purposes. For example, the MR images may include cardiac MR images and may be used to train a machine-learning model for removing motion artifacts from the cardiac MR images.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings.

Figure 1:
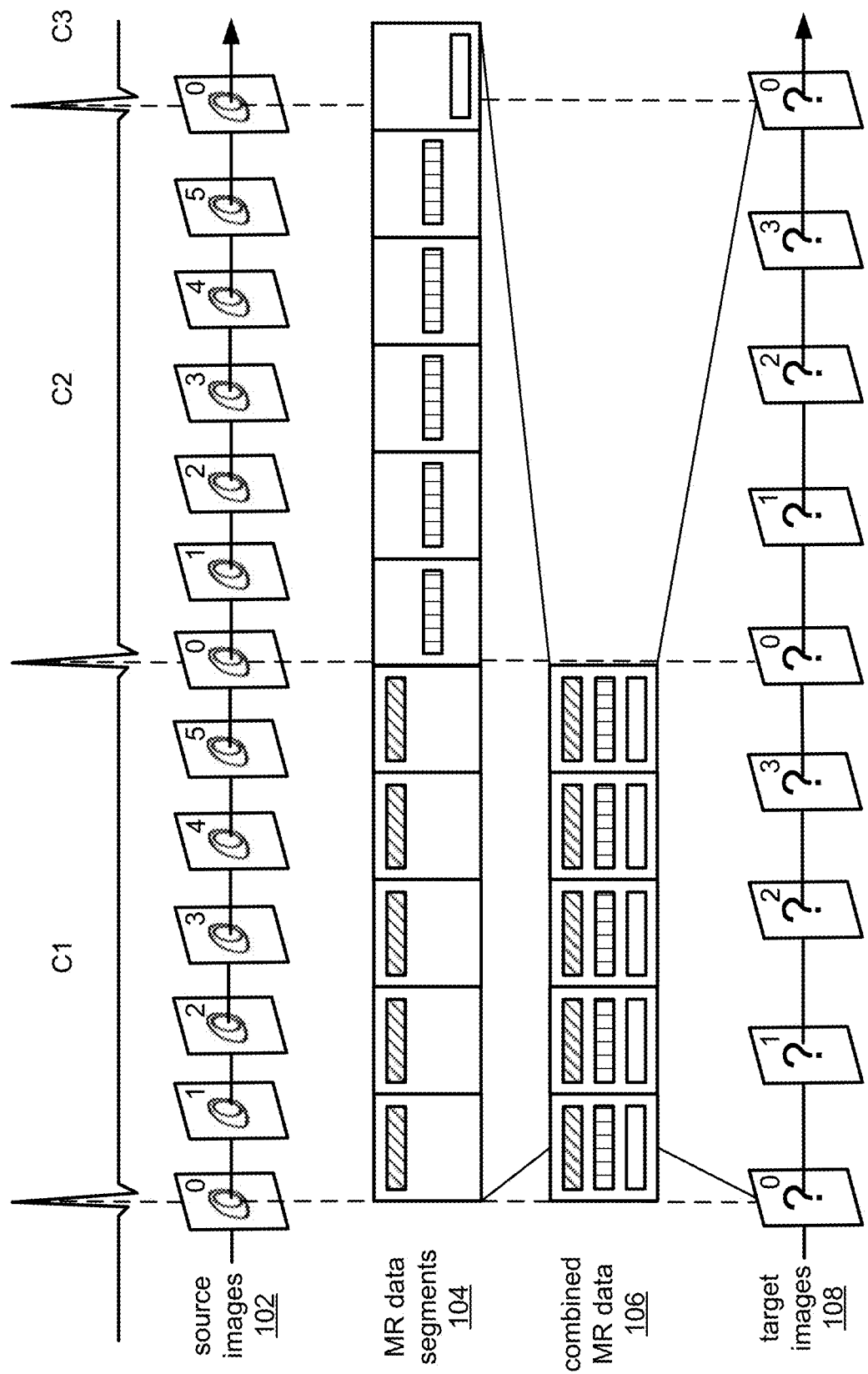
FIG. 1 is a block diagram illustrating an example framework for simulating motion artifacts in magnetic resonance (MR) images in accordance with one or more embodiments described herein.

FIG. 1 is a block diagram illustrating an example framework for simulating motion artifacts in magnetic resonance (MR) images. As shown, the simulation may be performed based on a set of source MR images 102 that is substantially free of the motion artifacts, and may involve one or more of the following operations: deriving at least one MR data segment 104 for each of multiple physiological cycles (e.g., C1, C2, C3, etc.) of a scanned object based on the source MR images 102 (or a modified version of the source MR images 102) associated with the physiological cycle, combining the MR data segments 104 derived for the multiple physiological cycles (e.g., C1, C2, C3, etc.) to obtain a simulated MR data set 106, and/or generating target MR images 108 based on the simulated MR data set (e.g., using selected portions of the MR data set) such that the MR target images 108 may exhibit one or more motion artifacts injected during the aforementioned operations.

The source MR images 102 may include a single image, a set of images, a cine video (e.g., comprising multiple MR images), and/or the like. The image(s) may be obtained from various sources, including, for example, from a magnetic resonance imaging (MRI) device, from a database storing patient imaging records, etc. Each of the source MR images 102 may be associated with a time spot (e.g., a position along a time axis) and may represent a state (e.g., a motion state M) of the scanned object at the time spot. For example, the source images 102 may include N images captured during a physiological cycle (e.g., a complete cycle of cardiac contraction or an RR interval) of the scanned object (e.g., the heart) and as such may represent respective motion states (M0, M1, M2, . . . MN) of the scanned object in the physiological cycle (e.g., the time intervals between neighboring motion states may reflect a temporal resolution of the source images). As another example, the set of source MR images 102 may include multiple sub-sets of source MR images, where each sub-set of source MR images may be associated with one of the multiple physiological cycles (e.g., C1, C2, C3, etc.). These sub-sets of source MR images may be parts of an original image set acquired to facilitate the motion simulation, or they may be created (e.g., replicated) during the motion simulation process. For instance, an original image set obtained for the motion simulation may include MR images associated only with physiological cycle C1, and as a part of the motion simulation process, the original MR images may be further associated with (e.g., replicated for) physiological cycles C2, C3, etc.

Motion artifacts may be introduced into the target images 108 during one or more of the stages shown in FIG. 1. These motion artifacts may include, for example, patient bulk movements, respiratory motions, irregular heartbeats, acquisition related artifacts (e.g., hardware errors), etc. As an example, artifacts caused by respiratory motions may be introduced by deforming the source MR images 102 based on artificially created motion events (e.g., a motion pattern) that represent the respiration, before deriving the MR data segments 104 based on the deformed source MR images (e.g., a modified version of the source MR images). As another example, the duration and/or number of physiological cycles used in the motion simulation may be manipulated to emulate motions that may occur during a practical MRI procedure. Such motions may include, for example, ECG mis-triggering, ECG false-triggering, irregular heartbeats (e.g., such as atrial fibrillation and premature ventricular contraction), etc. Greater details of these artifact injection techniques will be provided below, e.g., with reference to FIGS. 3 and 4.

The MR data segments 104 may include sub-sets of MR data segments, each derived for a respective one of the multiple physiological cycles (e.g., C1, C2, C3, etc.) and including k-space information that represents the spatial frequency information of the scanned object in two or three dimensions (e.g., the k-space may be covered by phase and frequency encoding data). The relationship between the k-space data segments and the source images may be defined by Fourier Transformation such as Fast Fourier Transformation (FFT). As such, the sub-set of MR data segment associated with a specific physiological cycle may be derived by applying FFT to the sub-set of source MR images or a modified version of the sub-set of source MR images associated with the physiological cycle. The data segments thus obtained may resemble those acquired during a practical MRI procedure. For example, with 2-dimensional (2D) Fourier transform, a line in the derived MR data segments may correspond to a digitized MR signal at a particular phase encoding level, and each digitized data point of the MR signal may be represented by a complex number, with real and imaginary components, or be defined as having a magnitude and phase. The positions of the digitized data points in k-space may be directly related to the gradient across the object being imaged. So, as the gradient changes over time, the k-space data may be sampled in a trajectory through Fourier space.

Figure 2:
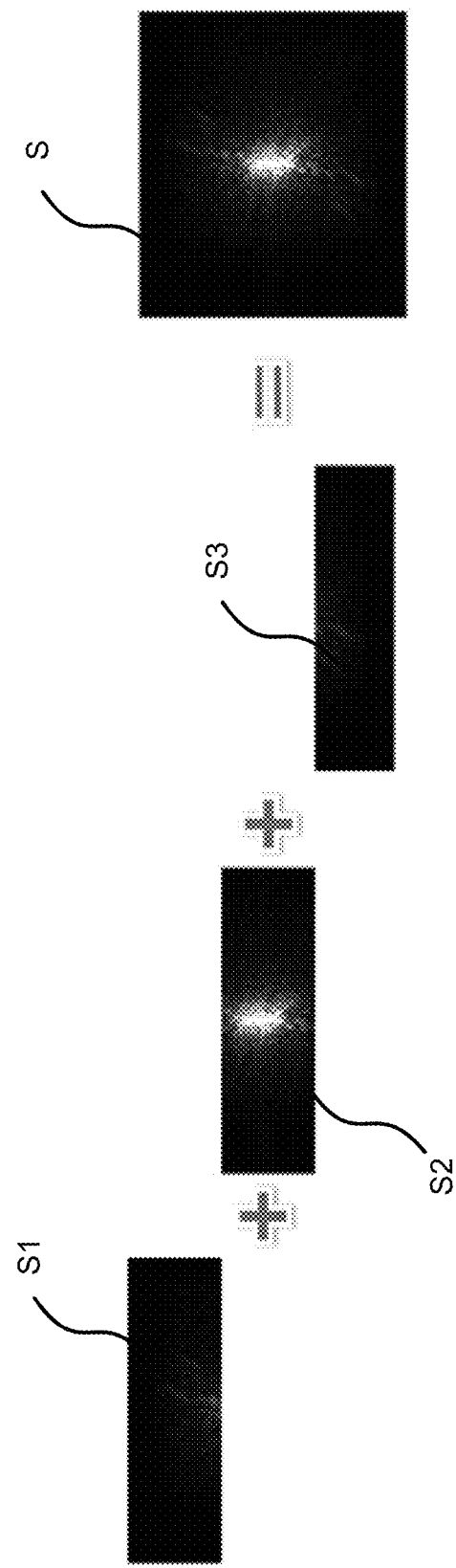
FIG. 2 is a block diagram illustrating an example of simulating MR signals based on segmented MR data in accordance with one or more embodiments described herein.

Because only a limited number of views of the scanned object may be available from each sub-set of source MR images (e.g., the number of views per segment (NVS) may be limited), two or more of the MR data segments 104 derived for the multiple physiological cycles may be combined into a simulated MR data set 106 to fill a portion (e.g., a desired portion) or the entirety of the k-space. The views described herein may correspond to MRI readout lines or lines in a 2D MR data space, which may be vertical, horizontal, or oblique. FIG. 2 illustrates an example in which MR data segments S1, S2, and S3 corresponding to physiological cycles C1, C2, and C3 are combined to obtain a set of simulated MR data, S, that covers (e.g., substantially) the entire k-space. Various techniques may be used to perform the combination (e.g., filling a desired portion or the entirety of the k-space), including, for example, those based on a row-by-row or line-by-line Cartesian method or those based on spiral and radially oriented trajectories. The timing of the MR data segments 104 (e.g., when the MR data segments are acquired) may be simulated and the MR data segments may be interpolated (e.g., based on simulated timing of the MR data segments and/or the timing of the source images 102) to simulate k-space signal acquisition in real practice (e.g., the number of target images generated using the framework described herein may be different from the number of source images).

Reverting to FIG. 1, the target MR images 108 may be generated by applying inverse FFT to the simulated MR data 106 (e.g., to selected portions of the MR data 106) and/or incorporating coil sensitivity (e.g., via one or more coil sensitivity maps) into the image generation process. For example, the image generation (e.g., image reconstruction) may include obtaining the product (e.g., via multiplication) of the complex conjugate of the coil sensitivity of each coil and an MR image obtained via the coil, and adding the products obtained for all of the coils, e.g., as illustrated below:

$$m = \Sigma_{i=1}^{n} \text{conjugate}(csm_i) * m\_i$$

where m may represent a coil-combined image, n may represent the number of coils, i may represent a coil index, csm_i may represent the coil sensitivity map of the i-th coil, and m_i may present the MR image obtained via the i-th coil.

The coil sensitivity described herein may resemble that of a single coil (e.g., multiple coils combined to derive coil-combined images) or multiple coils such as multiple phased-array coils used in a practical MRI procedure. In examples (e.g., if the MR data comprise complex-valued data elements), a coil sensitivity map may be determined based on the source images 102 and/or the simulated MR data 108 (e.g., k-space information) using various techniques. For instance, the coil sensitivity map of the i-th coil, csm_i, may be determined using a sum-of-squares method based on the following equation: csm_i=m_i/m_sos, where m_i may represent an MR image captured using the i-th coil, m_sos may be equal to $sqrt(\Sigma_{i=1}^{n} abs(m\_i)^2)$, and n may represent the number of coils being simulated. In examples (e.g., if the MR data include only magnitude values), a coil sensitivity map may be simulated, e.g., as a function of the distance from the coil center to a pixel location. For instance, if an image pixel is at location (x, y, z) and the coil center (e.g., in the same coordinate system) is at (a, b, c), then the coil sensitivity at (x, y, z) may be determined as $$\left(\frac{1}{r}\right)^3,$$

where $r=sqrt((x-a)^2+(y-b)^2+(z-c)^2)$. In examples, portions of the k-space data may be interpolated to derive additional target MR images so as to increase the temporal resolution of the target images (e.g., continuous rather than discrete image frames may be generated).

Figure 3:
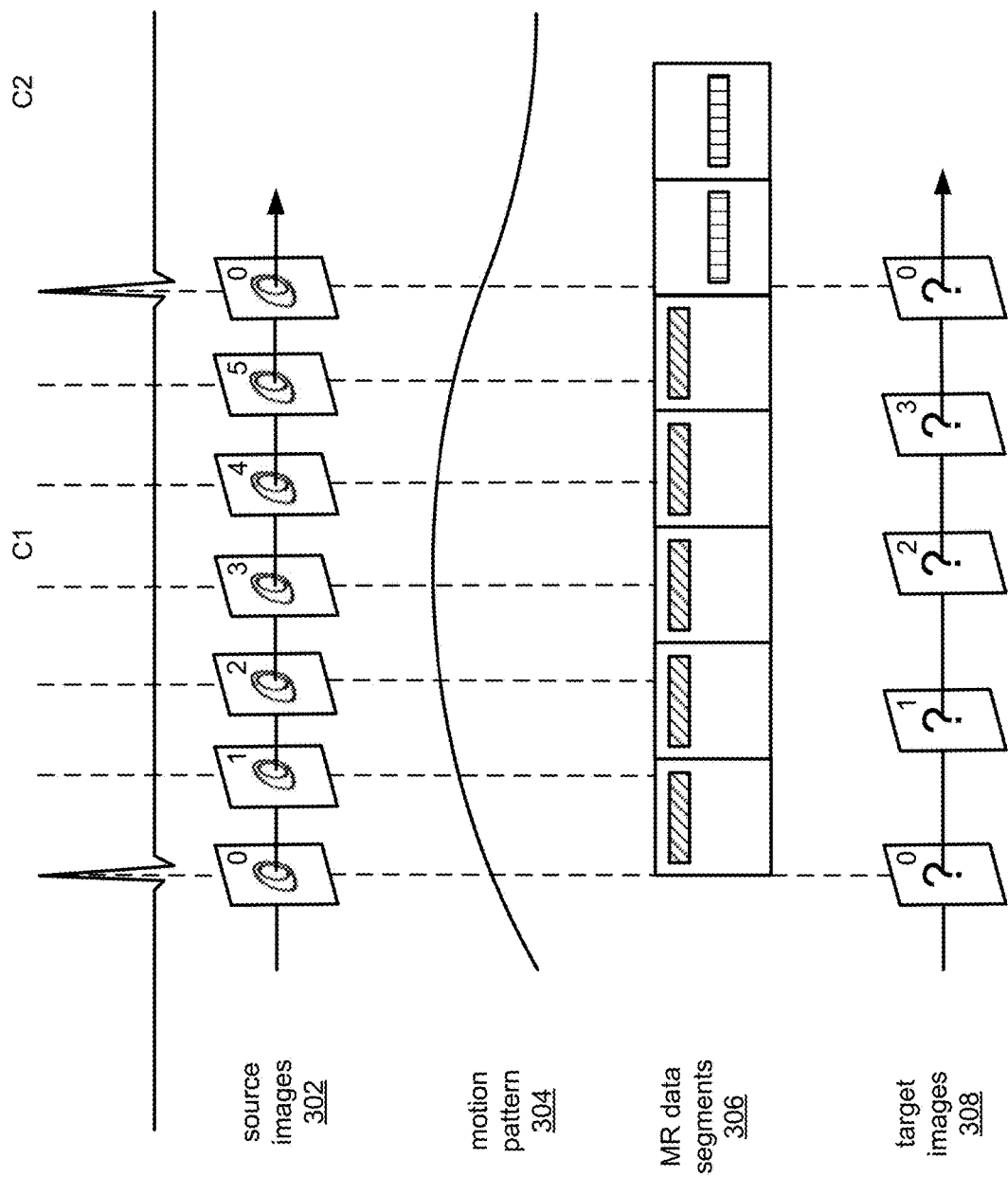
FIG. 3 is a block diagram illustrating an example of incorporating motion dynamics (e.g., motion artifacts) into MR images in accordance with one or more embodiments described herein.

As described herein, motion artifacts may be introduced by deforming the source MR images 102 based on artificially created motion events, by simulating the timing of physiological cycles and manipulating parameters (e.g., durations) of the physiological cycles to emulate artifacts caused by ECG mis-triggering, ECG false-triggering, and/or irregular heartbeats, etc. FIG. 3 illustrates an example of incorporating motion dynamics (e.g., motion artifacts) into MR images. The simulation may be performed based on a set of source MR images 302 that is substantially free of motion artifacts. These source MR images may be captured within a physiological cycle C1 (e.g., a complete cycle of cardiac contraction) of the scanned object and each image may be associated with a respective time spot within the physiological cycle. To inject motion artifacts into these source images, a motion pattern 304 may be created in the temporal direction of the source images 302. In examples, the motion pattern may include a breathing pattern (e.g., shown in FIG. 3) that represents the respiratory motions of a patient along a time axis. In examples, the motion pattern may represent irregular heartbeats (e.g., when the heart does not complete a contraction cycle), which may be simulated by reordering the source images in the temporal direction (e.g., the reordered images may correspond to motion states M0, M1, MN instead of M0, M1, M2 . . . MN) or by artificially inserting additional motion states (e.g., by interpolating two or more neighboring source images) into the source image set.

The motion dynamics or artifacts represented by the motion pattern 304 may be incorporated into the source images 302 by deforming the source images according to the motion pattern. For example, a breathing pattern shown in FIG. 3 may be represented by a parameterized motion model and the motion pattern 304 may include a set of motion curves each giving the value of one of the motion model's parameters as a function of time (e.g., matching the time spots or time positions of the source images 302). In examples, the motion model may be a translational shift model that mimics respiratory motions. Such a model may utilize a sinusoidal function that comprises a frequency component f and an amplitude component a, e.g., in the form of shift=a*sin(ft). In this equation, the frequency component f may represent the breathing frequency, the amplitude component a may represent the extent of the breathing motion, t may represent a specific time spot, and shift may represent the distance shifted by an image (e.g., an entire image) in a foot-head direction (e.g., which may be the main motion direction of breathing during MR short-axis imaging) at time t (e.g., different values may be set for a and f for different physiological settings or applications).

Based on the model and motion curves, various image deformation and/or registration techniques may be employed to modify the source images 302 such that the motion dynamics associated with the motion pattern 304 may be reflected in a modified version of the source images 302. These image deformation and/or registration techniques may include, for example, affine transformation, rigid translation, non-rigid translation, or a combination thereof.

Once the source images 302 have been modified to incorporate a desired motion artifact, the modified version of the source images may be used to derive corresponding MR data segments 306 for the concerned physiological cycle C1. As described herein, the derivation may be performed by applying Fast Fourier Transformation to the modified source images. Furthermore, the source images 302 may be associated with additional physiological cycles (e.g., C2 shown in FIG. 3) and be deformed based on the motion pattern 304 for those physiological cycles. Correspondingly, respective MR data segments may be derived for the additional physiological cycles before the data segments are merged (e.g., line by line or row by row) to obtain a simulated MR data set (e.g., digitized MR signals). The simulated MR data set (e.g., k-space data) may then be used to generate target MR images 308 that exhibit the motion artifacts injected by the motion pattern 304. Since the MR data used to generate the target images may be assembled from k-space segments across multiple physiological cycles and the k-space segments may be further interpolated to fill a portion or the entirety of the k-space, the target MR images 308 may be generated at a desired temporal resolution (e.g., at any temporal resolution or any time intervals) to demonstrate the artifacts indicated by the motion pattern 304.

Figure 4:
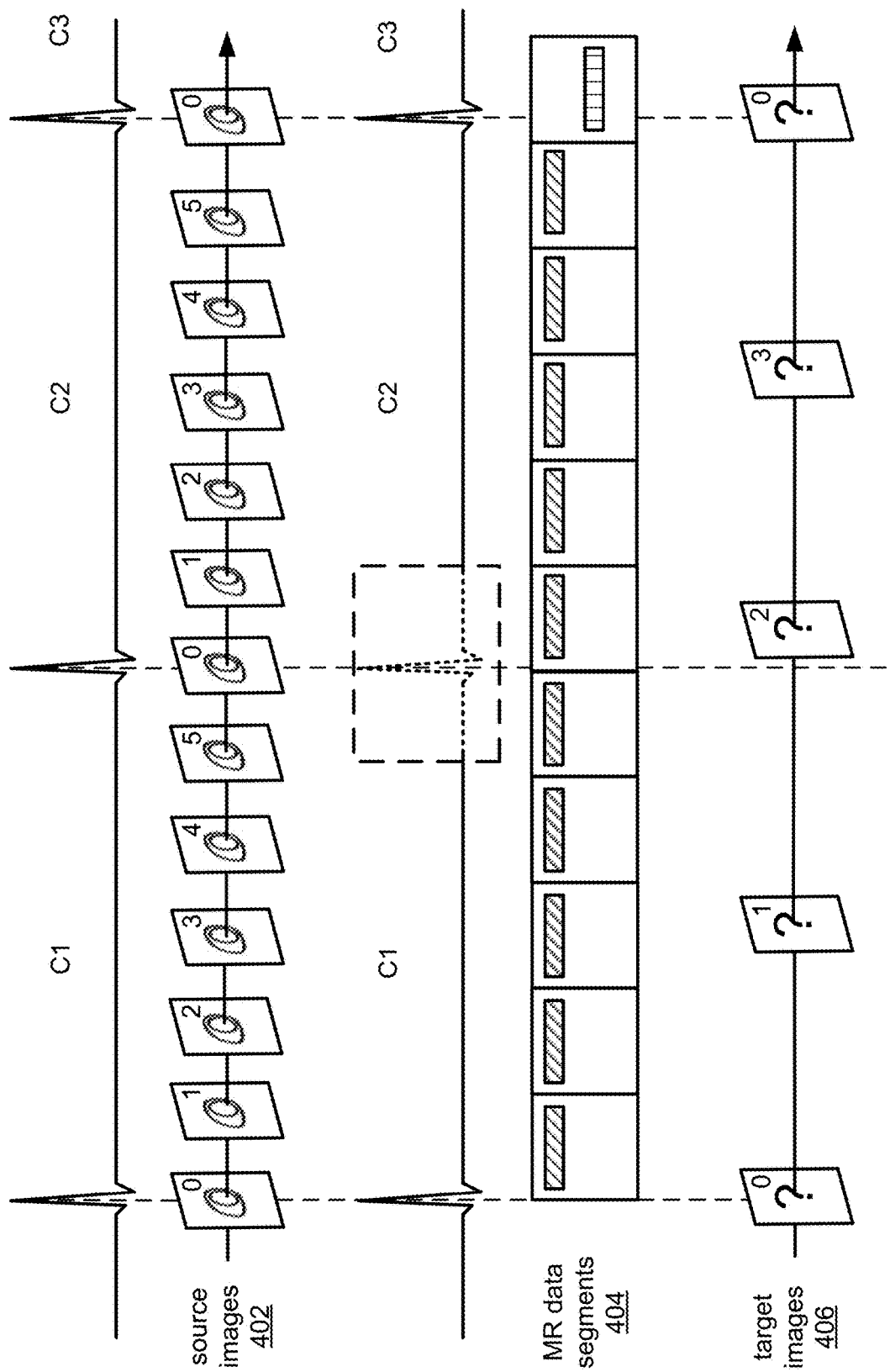
FIG. 4 is a block diagram illustrating an example of simulating motion artifacts in MR images by controlling the manner in which the MR images are generated.

FIG. 4 illustrates another example of simulating motion artifacts in MR images. Similar to the example shown in FIG. 3, the motion simulation may be performed based on a set of source MR images 402 that is substantially free of the motion artifacts. The source MR images may be grouped into multiple sub-sets of images each associated with a physiological cycle. The physiological cycles (e.g., C1, C2, C3, etc.) may be created to simulate the timing of R waves in an ECG procedure and as such the physiological cycles C1, C2, C3, etc. may correspond to RR intervals in a ECG graph (e.g., an RR interval may represent the time elapsed between two successive R-waves of the QRS signal on an electrocardiogram). Based on the sub-sets of images associated with the multiple physiological cycles, respective MR data segments 404 may be derived for the multiple physiological cycles and combined to obtain a simulated MR data set (e.g., digitized MR signals) that covers (e.g., substantially) a portion (e.g., representing a under-sample situation)

or the entirety (e.g., representing a fully-sample situation) of the k-space. The simulated MR data set may then be used to generate a sequence of target MR images 406 and, by controlling the manner in which the target MR images 406 are generated (e.g., controlling which portion of the MR data set is used to generate a target image), certain motion artifacts may be injected into the target images. For example, to simulate a mis-triggering artifact such as an ECG mis-trigger, the target images 406 may be distributed across (e.g., associated with) multiple of the physiological cycles (e.g., across RR intervals C1 and C2) instead of one such cycle so that the sequence of target images appears to have been taken with a missed trigger between C1 and C2.

Figure 5B:
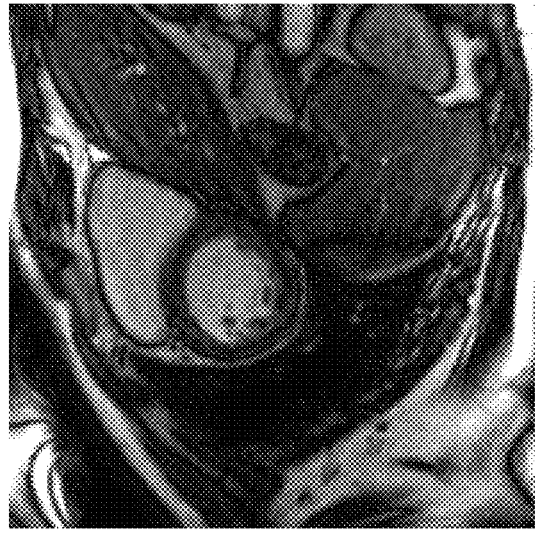
FIG. 5B is an example MR image comprising a respiratory artifact simulated in accordance with one or more embodiments described herein.
Figure 5A:
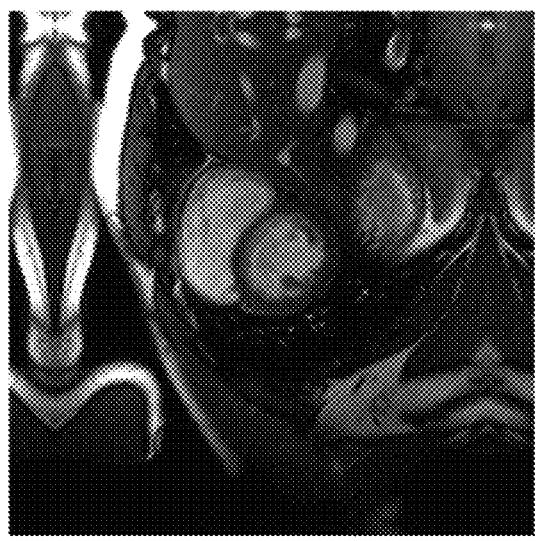
FIG. 5A is an example MR image comprising a mis-triggering artifact simulated in accordance with one or more embodiments described herein.

FIGS. 5A and 5B show example MR images with a simulated mis-triggering artifact and a simulated respiratory artifact, respectively. It should be noted that although cardiac MRI (cMRI) is used herein to describe the proposed motion simulation techniques, cMRI (e.g., retrospective triggering cine cMRI) only represents an example area where the proposed techniques may be deployed. Other MRI procedures (e.g., brain, abdomen, etc.) may also benefit from the proposed techniques. It should also be noted that what is embodied in the examples provided herein is a framework for simulating motion artifacts in MR images. The types of artifacts that may be generated using the framework are not limited to those described in the examples and may include others not specifically listed herein.

Figure 6:
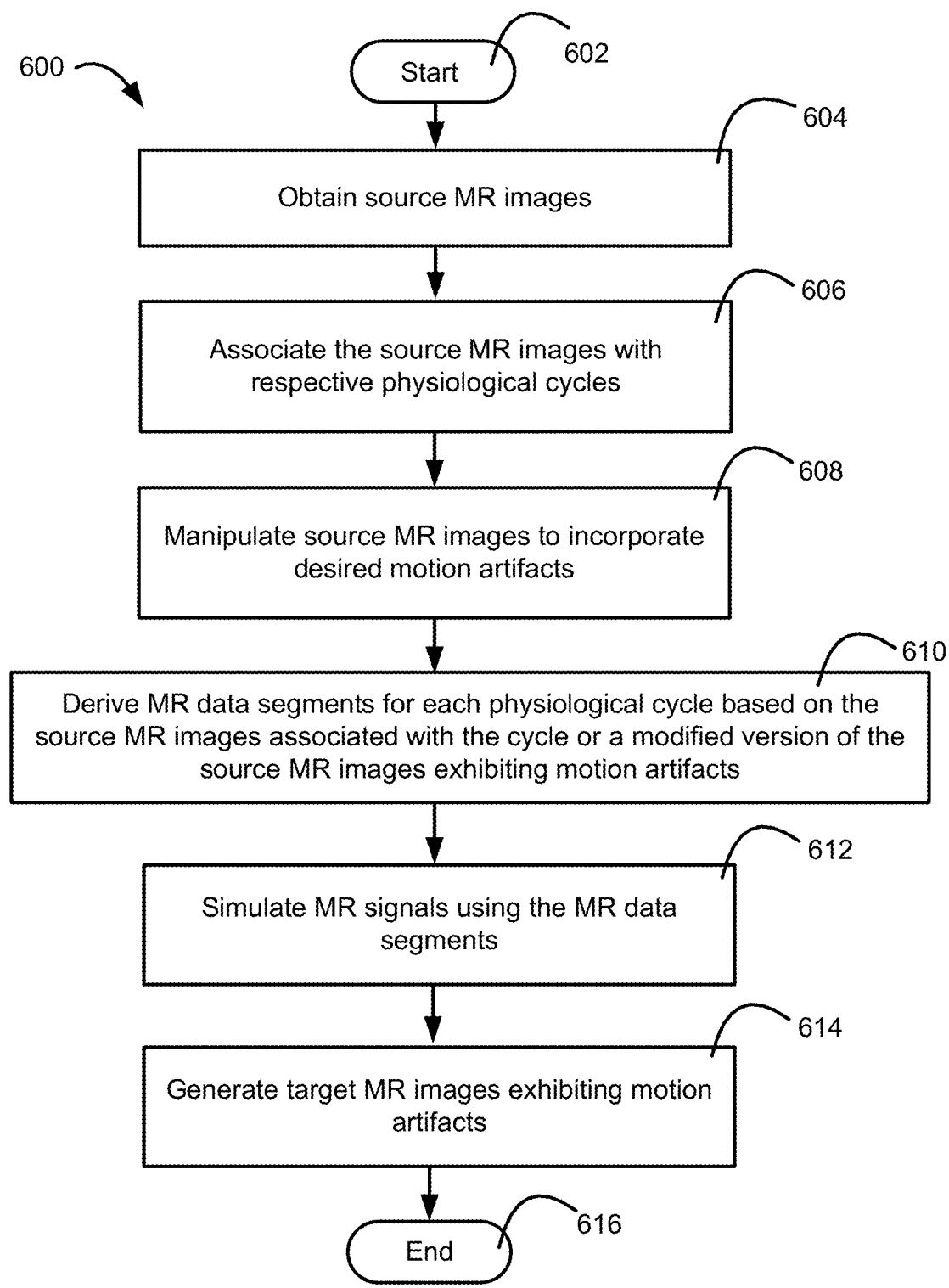
FIG. 6 is a flow diagram illustrating an example process for simulating motion artifacts in MR images in accordance with one or more embodiments described herein.

FIG. 6 is a flow diagram illustrating an example process 600 for simulating motion artifacts in MR images. The process may start at 602, and at 604, a set of source MR images (e.g., a single MR image, multiple MR images, a cine video, etc.) substantially free of motion artifacts may be obtained. The source images may be obtained, for example, from an MRI procedure, a database storing patient imaging records, etc. Each of the source images may be associated with a time spot or time position, and the entire set of images may span over one or more physiological cycles (e.g., RR intervals). For example, the set of source MR images may be originally associated with (e.g., captured within) a first physiological cycle and, as a part of the motion simulation process 600, may be associated with additionally physiological cycles at 606. At 608, the source MR images may be manipulated to incorporate a motion pattern (e.g., representing certain motion artifacts caused by respiratory motions, irregular heartbeats, etc.). In examples, the motion artifacts may be injected into the source MR images by deforming (e.g., via affine, rigid, or non-rigid transformation) the source images based on the motion pattern. In examples, the artifacts may be simulated by temporally reordering at least a portion of the source images or by artificially inserting additional MR images into the source image set (e.g., based on an interpolation of neighboring source images).

At 610, MR data segments may be derived for each of the physiological cycles based on the source MR images or a modified version of the source MR images (e.g., when motion artifacts are injected to the source images) associated with the physiological cycle. The MR data segments may be derived, for example, by applying Fourier Transformation (e.g., FFT) to the source MR images to obtain k-space information that represents the spatial frequency and/or phase information of the object scanned in the source MR images. At 612, the MR data segments derived for the physiological cycles may be combined to obtain a simulated MR data set (e.g., digitized MR signals) mimicking that acquired from a practical MRI procedure. In examples, the combining of the MR data segments may include merging the MR data segments row-by-row or based on spiral and/or radially oriented trajectories. In examples, the combining of the MR data segments may include interpolating the MR data segments to simulate top-down sampling of the MR signals.

Once obtained, the simulated MR data set may be used at 614 to generate one or more target MR images that include a certain motion artifact. As described herein, the motion artifact may be incorporated into a modified version of the source MR images from which one or more MR data segments may be derived. The motion artifacts may also be created, for example, by controlling the manner in which the target MR images are generated. For instance, each of the target MR images may be generated using a selected portion of the MR data set based on the desired motion artifact. As another example, to simulate an ECG mis-triggering artifact, the target images may be generated (e.g., distributed) across multiple of the physiological cycles so that the images appear to have been taken with a missed trigger between the physiological cycles. The motion simulation process 600 may then end at 616.

For simplicity of explanation, the operations involved in the motion simulation process 600 are depicted and described herein with a specific order. It should be noted, however, that these operations may occur in various orders, concurrently, and/or with other operations not presented or described herein. Furthermore, it should be noted that operations that may be included in the motion simulation process 600 may not all be depicted and described herein, and not all of the illustrated operations are required to be performed.

Figure 7:
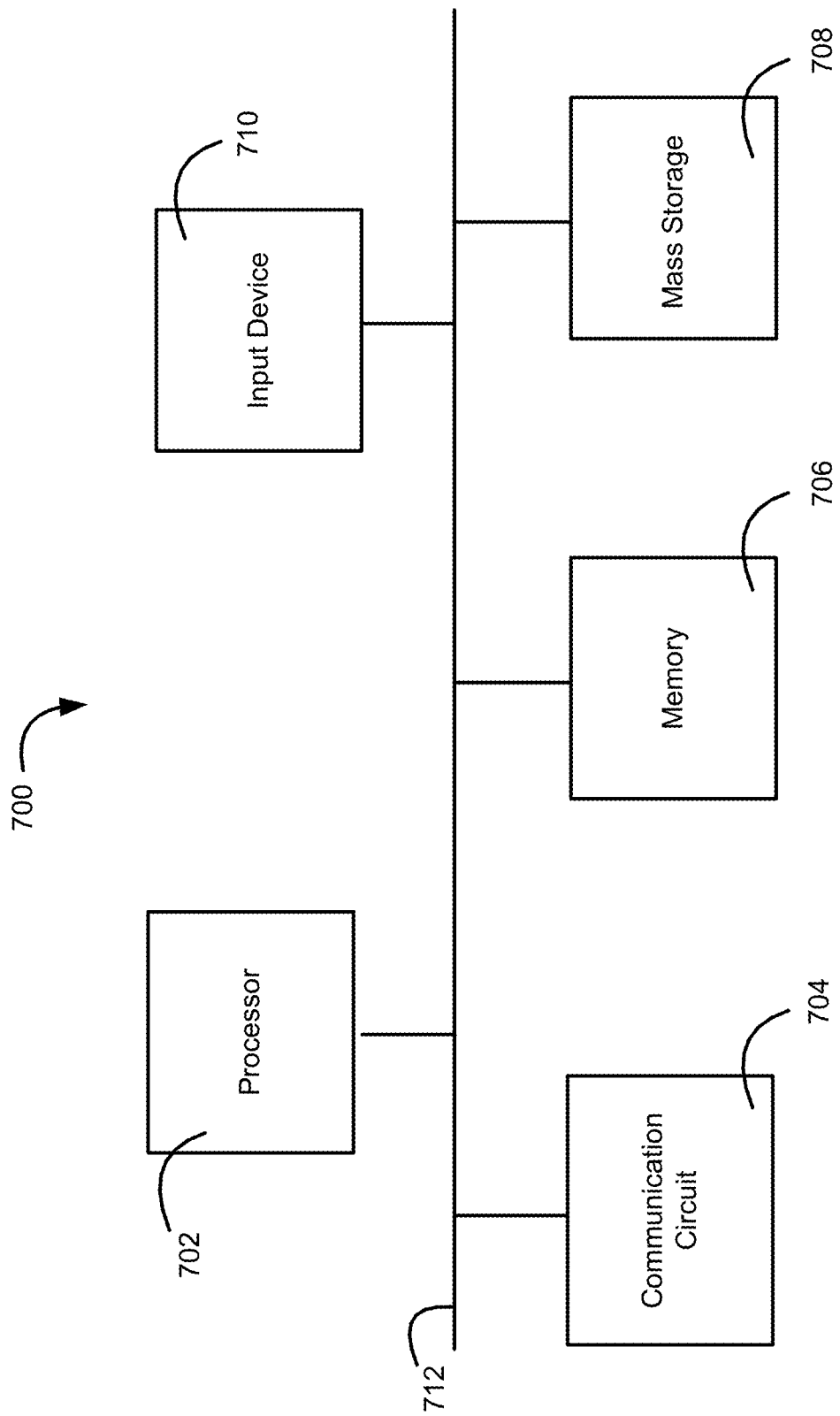
FIG. 7 is a block diagram illustrating example components of a motion simulator in accordance with one or more embodiments described herein.

The systems, methods, and/or instrumentalities described herein may be implemented using one or more processors, one or more storage devices, and/or other suitable accessory devices such as display devices, communication devices, input/output devices, etc. FIG. 7 is a block diagram illustrating an example motion simulator 700 that may be configured to perform one or more of the functions described herein. As shown, the motion simulator 700 may include a processor (e.g., one or more processors) 702, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The motion simulator 700 may further include a communication circuit 704, a memory 706, a mass storage device 708, an input device 710, and/or a communication link 712 (e.g., a communication bus) over which the one or more components shown in the figure may exchange information.

The communication circuit 704 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 706 may include a storage medium (e.g., a non-transitory storage medium) configured to store machine-readable instructions that, when executed, cause the processor 702 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EE- PROM)), flash memory, and/or the like. The mass storage device 708 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 702. The input device 710 may include a keyboard, a mouse, a voice-controlled input device, a touch sensitive input device (e.g., a touch screen), and/or the like for receiving user inputs to the motion simulator 700.

It should be noted that the motion simulator 700 may operate as a standalone device or may be connected (e.g., networked or clustered) with other computation devices to perform the functions described herein. And even though only one instance of each component is shown in FIG. 7, a skilled person in the art will understand that the motion simulator 700 may include multiple instances of one or more of the components shown in the figure.

The motion contaminated MR images simulated using the techniques described herein may be used to improve the quality and efficiency of various clinical applications. For example, the simulated MR images may be used to train an artificial neural network (ANN) to learn a model (e.g., a machine-learning (ML) model) for automatically removing motion artifacts from MR images acquired in a practical MRI procedure. Such a pre-trained ANN may be deployed (e.g., implemented) on one or more computing devices, which may be configured to receive an MR image of a scanned object that comprises a motion artifact and process the MR image through the pre-trained ANN to obtain an output image that is substantially free of the motion artifact.

Figure 8:
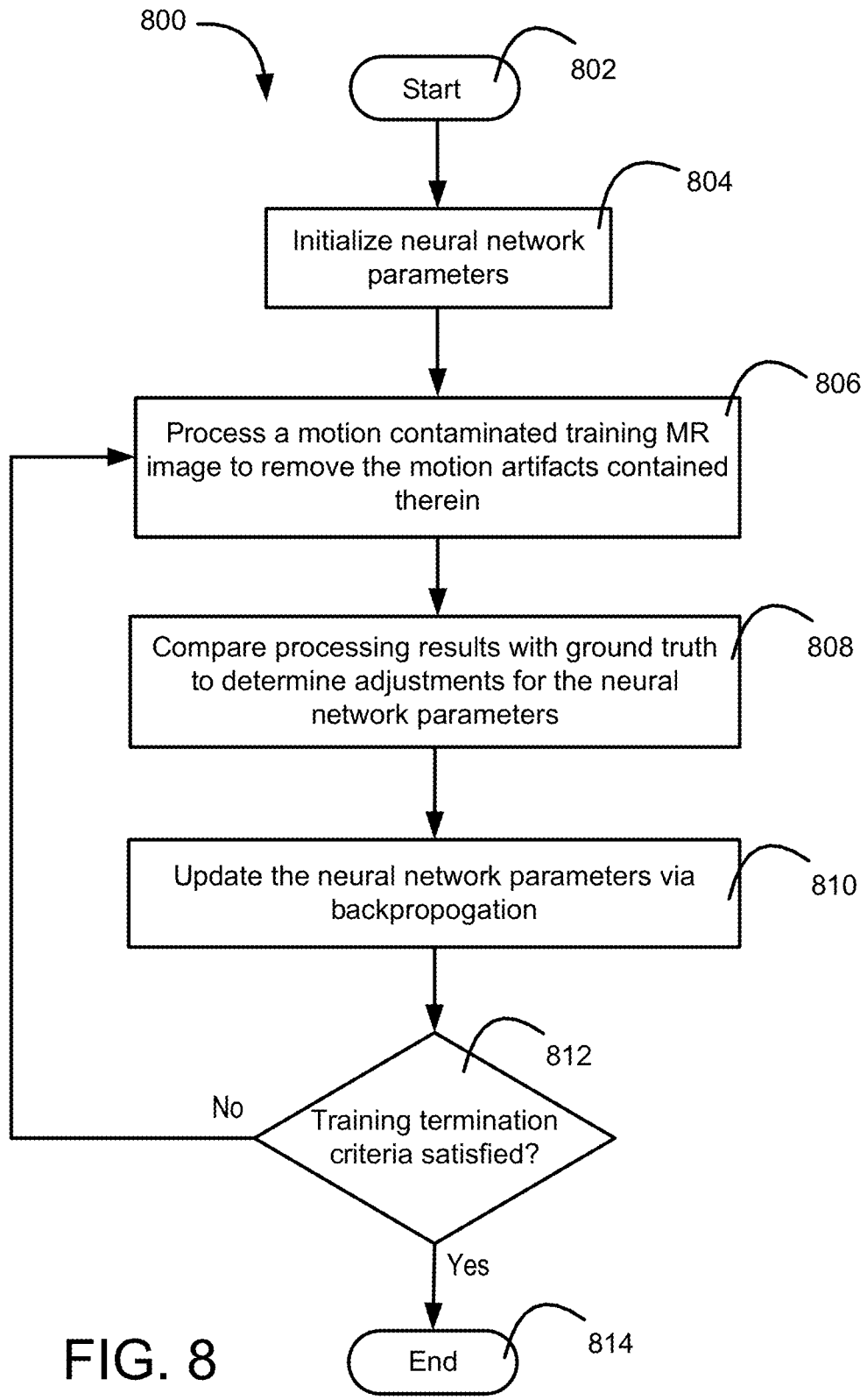
FIG. 8 is a flow diagram illustrating an example of using simulated MR images to train a neural network to perform motion artifact removal.

FIG. 8 illustrates a process 800 that may be used to train a neural network (e.g., a convolutional neural network (CNN)) to learn a motion artifact removal model based MR images generated using the techniques described herein. The process 800 may start at 802 and, at 804, initial parameters of the neural network (e.g., weights associated with various filters or kernels of the neural network) may be initialized. The parameters may be initialized, for example, based on samples collected from one or more probability distributions or parameter values of another neural network having a similar architecture. At 806, the neural network may receive a motion contaminated MR image generated using the simulation techniques described herein, and process the image through the various layers of the neural network to remove motion artifacts from the image (e.g., to predict a corresponding clean MR image free of the motion artifacts). At 808, the results of the processing may be compared to a ground truth to determine adjustments that need to be made to the presently assigned neural network parameters. The ground truth may a source MR image (e.g., the source MR image 102, 302 or 402 described herein) that was used to generate the motion contaminated image, and the adjustments to the network parameters may be determined based on a loss function (e.g., based on mean squared errors (MSE)) and a gradient descent (e.g., a stochastic gradient decent) associated with the loss function.

At 810, the neural network may apply the adjustments to the presently assigned network parameters, for example, via a backpropagation process. At 812, the neural network may determine whether one or more training termination criteria are satisfied. For example, the neural network may determine that the training termination criteria are satisfied if the neural network has completed a pre-determined number of training iterations, if the difference between the processing results and the ground truth values is below a predetermined threshold, or if the change in the value of the loss function between two training iterations falls below a predetermined threshold. If the determination at 812 is that the training termination criteria are not satisfied, the neural network may return to 806. If the determination at 812 is that the training termination criteria are satisfied, the neural network may end the training process 800 at 814.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process the are depicted and described herein, and not all illustrated operations are required to be performed.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A motion artifact simulator configured to inject motion artifacts associated with a medical procedure into medical magnetic resonance (MR) images, comprising:
   one or more processors configured to:
   obtain a set of source MR images of a scanned object, the set of source MR images being substantially free of motion artifacts and comprising multiple sub-sets of source MR images, each sub-set of source MR images being associated with one of multiple physiological cycles of the scanned object;
   derive at least one MR data segment for each of the multiple physiological cycles based on the sub-set of source MR images associated with the physiological cycle or a modified version of the sub-set of source MR images associated with the physiological cycle;
   obtain a MR data set based on the respective MR data segments derived for the multiple physiological cycles; and
   generate one or more target MR images based on the MR data set so that the one or more target MR images comprise a motion artifact.

2. The motion artifact simulator of claim 1, wherein the at least one MR data segment for each of the multiple physiological cycles is derived based on the modified version of the sub-set of source MR images associated with the physiological cycle, and wherein the one or more processors are configured to obtain the modified version of the sub-set of source MR images by modifying the sub-set of source MR images to incorporate a motion pattern associated with the motion artifact.

3. The motion artifact simulator of claim 2, wherein the one or more processors being configured to modify the sub-set of source MR images associated with each of the multiple physiological cycles to incorporate the motion pattern comprises the one or more processors being configured to deform the sub-set of source MR images based on a model that represents the motion pattern.

4. The motion artifact simulator of claim 2, wherein the one or more processors being configured to modify the sub-set of source MR images associated with each of the multiple physiological cycles to incorporate the motion pattern comprises the one or more processors being configured to reorder at least a portion of the set of source MR images or interpolate a portion of the set of source MR images to derive one or more additional source MR images.

5. The motion artifact simulator of claim 1, wherein the one or more target MR images are associated with at least two of the multiple physiological cycles.

6. The motion artifact simulator of claim 1, wherein the one or more processors being configured to generate the one or more target MR images based on the MR data set comprises the one or more processors being configured to select a portion of the MR data set and generate a target MR image based on the selected portion of the MR data set.

7. The motion artifact simulator of claim 1, wherein the one or more processors being configured to obtain the MR data set based on the respective MR data segments derived for the multiple physiological cycles comprises the one or more processors being configured to combine the MR data segments derived for the multiple physiological cycles.

8. The motion artifact simulator of claim 7, wherein the one or more processors being configured to combine the MR data segments derived for the multiple physiological cycles comprises the one or more processors being configured to interpolate at least a portion of the MR data segments to obtain the MR data set.

9. The motion artifact simulator of claim 1, wherein the at least one MR data segment derived for each of the multiple physiological cycles comprises k-space data, and wherein the one or more processors are configured to obtain the k-space data by applying Fast Fourier Transform (FFT) to the sub-set of source MR images associated with the each of the multiple physiological cycles or the modified version of the sub-set of source MR images associated with the each of the multiple physiological cycles.

10. The motion artifact simulator of claim 1, wherein the one or more processors being configured to generate the one or more target MR images based on the MR data set comprises the one or more processors being configured to generate each of the one or more target MR images by applying inverse Fast Fourier Transform (FFT) to at least a portion of the MR data set.

11. The motion artifact simulator of claim 10, wherein the one or more processors are configured to generate the one or more target MR images further based on one or more coil sensitivity maps.

12. The motion artifact simulator of claim 1, wherein the set of source MR images comprises cardiac MR images and the multiple physiological cycles comprise one or more cardiac intervals.

13. A method for injecting motion artifacts associated with a medical procedure into medical magnetic resonance (MR) images, the method comprising:

obtaining a set of source MR images of a scanned object, the set of source MR images being substantially free of motion artifacts and comprising multiple sub-sets of source MR images, each sub-set of source MR images being associated with one of multiple physiological cycles of the scanned object;

deriving at least one MR data segment for each of the multiple physiological cycles based on the sub-set of source MR images associated with the physiological cycle or a modified version of the sub-set of source MR images associated with the physiological cycle;

obtaining an MR data set based on the respective MR data segments derived for the multiple physiological cycles; and generating one or more target MR images based on the MR data set so that the one or more target MR images comprise a motion artifact.

14. The method of claim 13, wherein the at least one MR data segment for each of the multiple physiological cycles is derived based on the modified version of the sub-set of source MR images associated with the physiological cycle, and wherein the modified version of the sub-set of source MR images is obtained by deforming the sub-set of source MR images based on a model that presents a motion pattern associated with the motion artifact.

15. The method of claim 13, wherein the at least one MR data segment for each of the multiple physiological cycles is derived based on the modified version of the sub-set of source MR images associated with the physiological cycle, and wherein the modified version of the sub-set of source MR images is obtained by reordering at least a portion of the set of source MR images or interpolating a portion of the set of source MR images to derive one or more additional source MR images.

16. The method of claim 13, wherein the MR data set is obtained by combining the respective MR data segments derived for the multiple physiological cycles and wherein generating the one or more target MR images based on the MR data set comprises selecting a portion the MR data set and generating a target MR image based on the selected portion of the MR data set.

17. The method of claim 13, wherein the at least one MR data segment derived for each of the multiple physiological cycles comprises k-space data obtained by applying Fast Fourier Transform (FFT) to the sub-set of source MR images associated with the each of the multiple physiological cycles or the modified version of the sub-set of source MR images associated with the each of the multiple physiological cycles, and wherein each of the one or more target MR images is generated by applying inverse FFT to at least a portion of the MR data set.

18. The method of claim 17, wherein each of the one or more target MR images is generated further based on one or more coil sensitivity maps.

19. The method of claim 13, further comprising using the one or more target MR images to train a machine-learning model for removing motion artifacts from an MR image.

20. A computer-implemented method for processing medical magnetic resonance (MR) images, the method comprising:

receiving an MR image of a scanned object, wherein the MR image comprises a motion artifact; and processing the MR image through an artificial neural network to obtain an output image that is substantially free of the motion artifact, wherein the artificial neural network is pre-trained using computer-generated MR training images to remove the motion artifact from the MR image, and the MR training images comprise motion artifacts created by at least:

obtaining a set of source MR images of the scanned object, the set of source MR images being substantially free of the motion artifacts and comprising multiple sub-sets of source MR images, each sub-set of source MR images being associated with one of multiple physiological cycles of the scanned object;

deriving at least one MR data segment for each of the multiple physiological cycles based on the sub-set of source MR images associated with the physiological cycle or a modified version of the sub-set of source MR images associated with the physiological cycle;

obtaining an MR data set based on the respective MR data segments derived for the multiple physiological cycles; and generating the MR training images based on the MR data set, wherein the generating comprises manipulating at least a portion of the MR data set to inject the motion artifacts into the MR training images.

* * * * *